United States Patent
Landry et al.

(10) Patent No.: US 11,946,104 B2
(45) Date of Patent: Apr. 2, 2024

(54) NON-INVASIVE PRENATAL TESTING AT EARLY STAGE OF PREGNANCY

(71) Applicant: BillionToOne, Inc., Menlo Park, CA (US)

(72) Inventors: Brian Landry, Redwood City, CA (US); Alexander Ni, Mountain View, CA (US)

(73) Assignee: BILLIONTOONE, INC., Menlo Park, CA (US)

( * ) Notice: Subject to any disclaimer, the term of this patent is extended or adjusted under 35 U.S.C. 154(b) by 0 days.

(21) Appl. No.: 16/923,005

(22) Filed: Jul. 7, 2020

(65) Prior Publication Data

US 2022/0010379 A1    Jan. 13, 2022

(51) Int. Cl.
| | |
|---|---|
| C12Q 1/68 | (2018.01) |
| C12P 19/34 | (2006.01) |
| C12Q 1/6869 | (2018.01) |
| C12Q 1/6883 | (2018.01) |

(52) U.S. Cl.
CPC ......... C12Q 1/6883 (2013.01); C12Q 1/6869 (2013.01); *C12Q 2600/156* (2013.01); *G01N 2800/387* (2013.01)

(58) Field of Classification Search
CPC . C12Q 1/6883; C12Q 2600/156; G16B 20/20
See application file for complete search history.

(56) References Cited

U.S. PATENT DOCUMENTS

| | | |
|---|---|---|
| 8,700,338 B2 | 4/2014 | Oliphant et al. |
| 9,447,453 B2 | 9/2016 | Rava et al. |
| 11,441,185 B2 | 9/2022 | Oliphant et al. |
| 2012/0190021 A1 | 7/2012 | Oliphant et al. |
| 2012/0214680 A1 | 8/2012 | Oeth et al. |

OTHER PUBLICATIONS

Peter Benn, et al. "Theoretical performance of non-invasive prenatal testing for chromosome imbalances using counting of cell-free DNA fragments in maternal plasma" Prenatal Diagnosis, 34, p. 778-783. (Year: 2014).*

Peiyong Jiang, et al. "FetalQuant: deducing fractional fetal DNA concentration from massively parallel sequencing of DNA in maternal plasma" Bioinformatics, vol. 28, Issue 22, Nov. 15, 2012, pp. 2883-2890 (Year: 2012).*

Peiyong Jiang, et al. "FetalQuant: deducing fractional fetal DNA concentration from massively parallel sequencing of DNA in maternal plasma" Bioinformatics, vol. 28, Issue 22, Nov. 2012, pp. 2883-2890 (Year: 2012).*

Heng Li, et al. "Fast and accurate short read alignment with Burrows—Wheeler transform" Bioinformatics. Jul. 15, 2009; 25(14): 1754-1760 (Year: 2009).*

Amin R, Mazloom, et al. "sample Specific Fetal Fraction Threshold for Non-Invasive Prenatal Testing", Poster No. 777 from Integrated Genetics (2017) (Year: 2017).*

Hui et al., "Fetal fraction and noninvasive prenatal testing: What clinicans need to know," Prenetal Diagnosis, vol. 40, No. 2, Jan. 28, 2020, pp. 155-163, XP055863870.

Ziza et al., "Determination of Fetal RHD Genotype Including the RHD Pseudogene in Maternal Plasma," Journal of Clinical Laboratory Analysis, vol. 13, No. 3, May 1, 2017, pp. e22052, XP055841172.

Avent, "RHD genotyping from maternal plasma: guidelines and technical challenges," Prenatal Diagnosis: Methos in Molecular Biology, vol. 444, Jan. 1, 2008, XP055864570.

Turner et al,. "Detection of fetal Rhesus D gene in whole blood of women booking for routine antenatal care," European Journal of Obstetrics & Gynecology and Reproductive Biology, vol. 108, No. 1, May 1, 2003, pp. 29-32, XP055011867.

\* cited by examiner

*Primary Examiner* — Stephen T Kapushoc
(74) *Attorney, Agent, or Firm* — Fenwick & West LLP

(57) ABSTRACT

A highly accurate non-invasive prenatal testing methodology that allows accurate fetal rhesus determination and fetal DNA fraction measurement in a single assay is provided. The disclosed testing may be administered as early as at week 10 of pregnancy and can be conveniently combined with prenatal genetic disease testing and detection.

16 Claims, 3 Drawing Sheets

NON-INVASIVE PRENATAL TESTING AT EARLY STAGE OF PREGNANCY

FIELD

Provided herein is a highly accurate non-invasive prenatal testing (NIPT) methodology that allows fetal rhesus determination and fetal DNA fraction measurement in a single assay. The disclosed NIPT may be administered as early as at week 10 of pregnancy and provides low-cost, reliable and specific fetal rhesus and fetal fraction determination, thus avoiding unnecessary administration of Rh immune globulin at a later stage of pregnancy.

BACKGROUND

Rhesus disease, also known as hemolytic disease of the fetus and newborn, is a condition in which antibodies in a pregnant woman's blood target and destroy her baby's blood cells. A pregnant mother may develop RhD sensitization if her fetus has an RhD-positive blood type and she has a rhesus blood group (D antigen) (RhD)-negative blood type. If the mother has developed RhD sensitization, subsequent pregnancies in which the fetus has an RhD-positive blood type may result in hemolytic disease with severe anemia in the fetus, and fetal demise.

Prophylactic standard of care requires administration of an Rh immune globulin (Rhogam) shot at week 28 of pregnancy as well as soon after childbirth to prevent RhD sensitization. However, bleeding events that may occur prior to Rhogam administration at week 28, as a result of miscarriage, amniocentesis or other complications during pregnancy may lead to Rh sensitization even when standard of care protocols are followed. In addition, Rhogam is needlessly administered to 40% of mothers whose unborn babies have an RhD-negative blood type.

There exist qPCR-based non-invasive prenatal testing (NIPT) of cell-free DNA that are administered during pregnancy to women that have an RhD-negative blood type, to establish the Rh status of the fetus and determine whether administration of Rhogam at week 28 of pregnancy is necessary. However, these tests become reliable only after week 20 of pregnancy and are plagued by poor performance.

Early pregnancy accurate determination of whether the fetus is at risk of developing antibody-mediated hemolysis as a consequence of RhD incompatibility between the mother and her unborn baby is therefore needed. The present application presents a solution to the aforementioned challenges by providing a non-invasive pregnancy test that makes use of next-generation sequencing to accurately determine the fraction of fetal cell-free DNA (cfDNA) in the maternal blood circulation and the Rh status of the fetus in a single assay at an early gestational stage. Although early in pregnancy only very small amounts of fetal cfDNA circulate in the maternal plasma, the disclosed test combines measurement of the fetal fraction via determination of polymorphic allele variations that are unique to the fetus, with next generation sequencing to quantify the amount of the RhD gene. It may therefore be administered as early as at week 10 of pregnancy with high reliability and low no-call rates. Moreover, the disclosed test is able to determine a wide range of different RhD genotypes, including RhD (i.e., RhD psi), which is not detected in single-plex qPCR assays. The disclosed NIPT has high performance, is low cost and it can be further used for pre-natal genetic defect detection.

SUMMARY

A method for accurate determination of fetal Rhesus D genotype and measurement of fetal fraction that can be performed in one assay at an early stage of pregnancy is provided.

In some embodiments, the method comprises: (i) collecting a blood sample from a pregnant woman subject; (ii) extracting cell-free DNA from the blood sample; (iii) performing multiplex polymerase chain reaction of the cell-free DNA to simultaneously amplify polymorphic allele loci and multiple RhD gene locations; (iv) sequencing amplified DNA; (v) identifying and selecting polymorphic paternal alleles to obtain a fetal fraction measurement; (vi) identifying and selecting amplified RhD gene regions to obtain quantitative fetal RhD data; and (vii) combining the fetal fraction measurement and the fetal RhD amount data into an algorithm to determine the fetal Rhesus D genotype.

The pregnant woman subject may be at a gestational stage 10 weeks or higher.

In some embodiments, the pregnant woman subject has Rhesus D negative genotype. In some embodiments, the pregnant woman subject has Rhesus RhD-CE-D genotype. In some embodiments, the pregnant woman subject has Rhesus D pseudogene (RHDψ) genotype.

The disclosed method may further comprise a step of quantifying fetal molecules in the RhD gene regions.

In some embodiments, the disclosed method may further comprise analyzing the blood sample to determine the fetus' sex.

In additional embodiments, the disclosed method may further comprise analyzing the blood sample to determine presence or absence of fetal aneuploidy for genetic disease detection. Genetic diseases that may be detected by the disclosed method may include, but are not limited to, Down syndrome, Edwards syndrome, Patau syndrome, Turner syndrome, and Klinefelter syndrome.

Additionally provided herein is a non-invasive method for accurate differentiation of fetal Rhesus D positive, fetal RhD negative, and fetal RHDψ genotype during pregnancy, wherein the method comprises: (i) collecting a blood sample from a pregnant woman subject; (ii) extracting cell-free DNA from the blood sample; (iii) amplifying cell-free DNA in at least one RhD gene location in Exon 4 or Exon 5 or Exon 6, which is expected to differ between RhD positive and RHDψ genotype; (iv) simultaneously amplifying cell-free DNA at a plurality of polymorphic allele loci; (v) sequencing amplified DNA; (vi) identifying and selecting polymorphic paternal alleles to obtain a fetal fraction measurement; (vii) classifying sequencing data from the RhD gene regions as belonging to RhD or RHDψ sequence; (vii) quantifying the levels of RhD and RHDψ; and (viii) combining fetal fraction measurement and levels of fetal RhD data and fetal RHDψ data into an algorithm to differentiate between fetal RhD positive, fetal RhD negative, and fetal RHDψ genotypes.

The pregnant woman subject may be at a gestational stage 10 weeks or higher.

In some embodiments, the pregnant woman subject has Rhesus D negative genotype. In some embodiments, the pregnant woman subject has Rhesus RhD-CE-D genotype. In some embodiments, the pregnant woman subject has Rhesus D pseudogene (RHDψ) genotype.

In some embodiments, the disclosed method may further comprise analyzing the blood sample to determine the fetus' sex.

In additional embodiments, the disclosed method may further comprise analyzing the blood sample to determine presence or absence of fetal aneuploidy for genetic disease detection. Genetic diseases that may be detected by the disclosed method may include, but are not limited to, Down syndrome, Edwards syndrome, Patau syndrome, Turner syndrome, and Klinefelter syndrome.

Also provided herein is a sequencing-based method for accurate determination of fetal Rhesus D genotype at an early stage of pregnancy, wherein the method comprises: (i) collecting a blood sample from a pregnant woman subject; (ii) extracting cell-free DNA from the blood sample; (iii) simultaneously amplifying multiple RhD gene locations; (iv) sequencing amplified DNA; (v) identifying and selecting amplified RhD gene regions to obtain quantitative fetal RhD data; and (vi) determining fetal Rhesus D genotype.

In some embodiments, the disclosed method may further comprise (vi) amplifying polymorphic allele loci; (vii) sequencing amplified DNA; and (viii) identifying and selecting polymorphic paternal alleles to obtain a fetal fraction measurement.

The pregnant woman subject may be at a gestational stage at 10 weeks or later in pregnancy.

In some embodiments, the pregnant woman subject has Rhesus D negative genotype. In some embodiments, the pregnant woman subject has Rhesus RhD-CE-D genotype. In some embodiments, the pregnant woman subject has Rhesus D pseudogene (RHDψ) genotype.

In some embodiments, the disclosed method may further comprise quantifying fetal molecules in the RhD gene regions. In some embodiments, the disclosed method may further comprise analyzing the blood sample to determine the fetus' sex. In some embodiments, the disclosed method may further comprise analyzing the blood sample to determine presence or absence of fetal aneuploidy for genetic disease detection. Genetic diseases that may be detected by the disclosed method may include, but are not limited to, Down syndrome, Edwards syndrome, Patau syndrome, Turner syndrome, and Klinefelter syndrome.

The foregoing and other features of the disclosure will become more apparent from the following detailed description of several embodiments, which proceeds with reference to the accompanying figures.

These data shows that fetal fraction measurement in combination with RhD detection is critical to implementing a high performing Rh NIPT.

Figure 2:
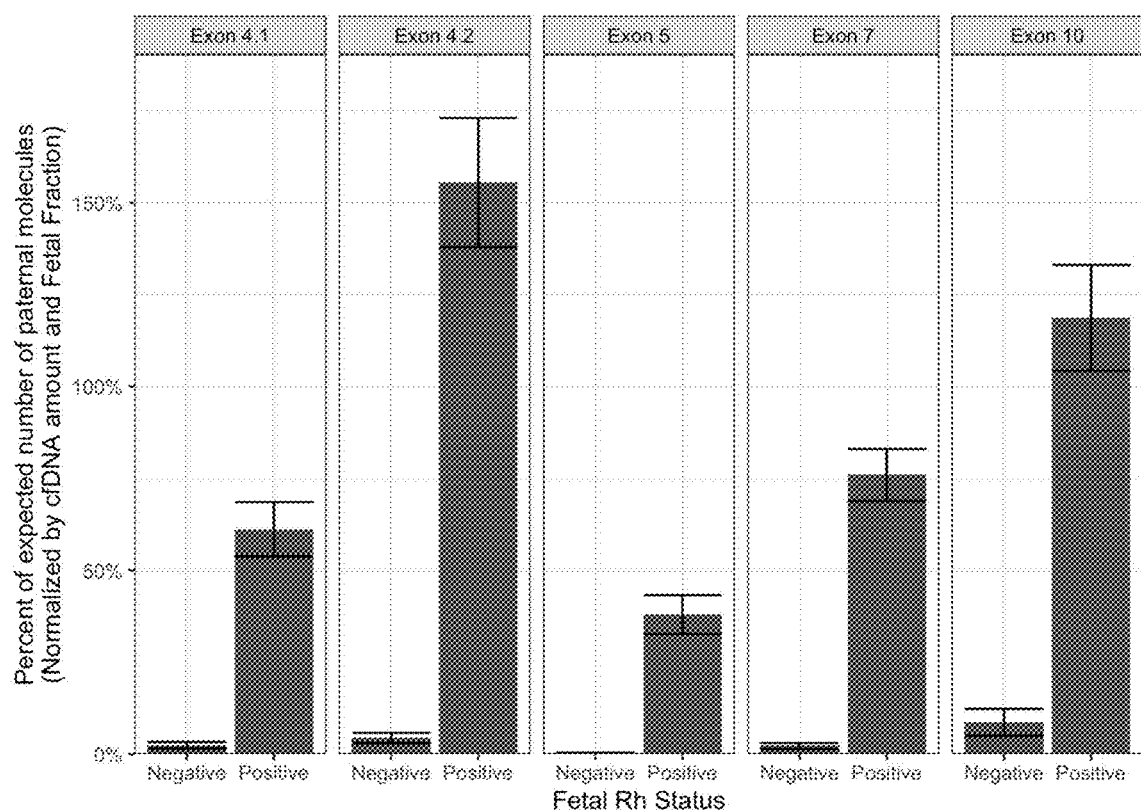

FIG. 2 shows the performance of the assay described in Example 1 for each of the 5 amplicons within the RHD gene in all tested samples. The bars represent the mean amount of RhD amplicon measured for each sample. Error bars represent the standard mean error for each sample. These data show the large difference in signal between RhD-negative fetal blood type and RhD-positive fetal blood type for each of the amplicons that were tested in this assay.

Figure 3:
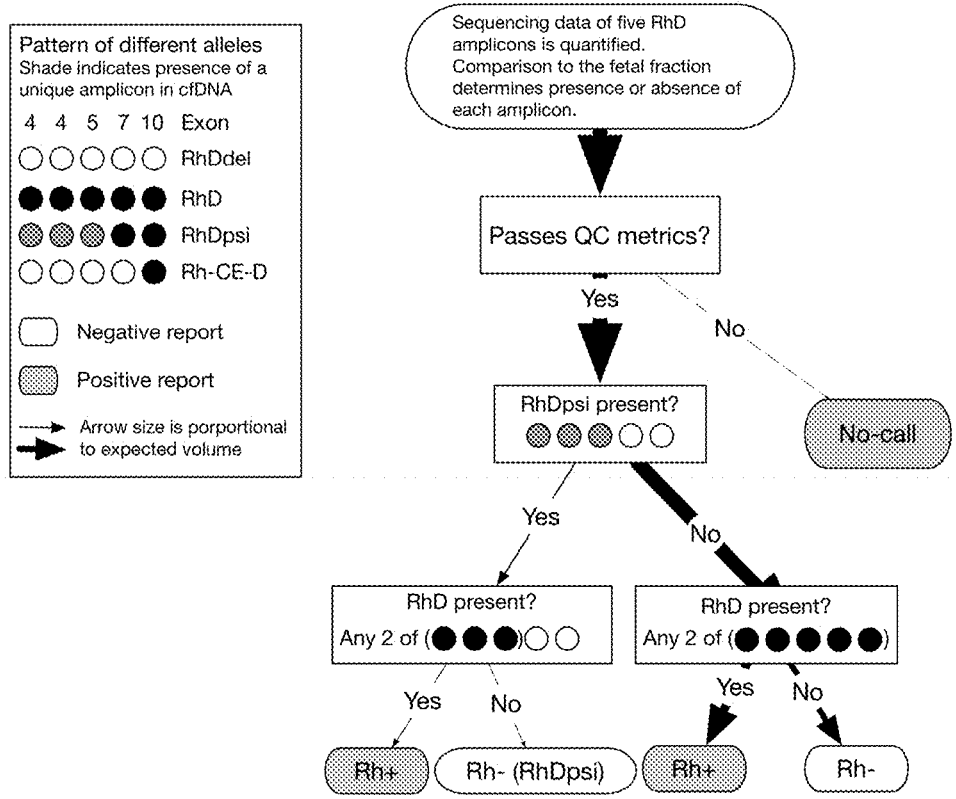

FIG. 3 shows an algorithm that was developed to differentially analyze samples for the presence of RhD when the RhD pseudogene psi variant is present. Data is analyzed as described in Example 1 and in FIG. 1 for unique amplicons generated by the RhD psi variant in two locations in exon 4 and in one location in exon 5. If the RhD psi sequence is detected as present in any of these locations the sample undergoes a separate set of statistical analyses that test for the presence of the Rh+RhD gene at locations only in exons 4 and exon 5. This is because the RhD psi gene contains sequence identical to the RhD gene in exons 7 and 10. The algorithm allows for accurate determination of fetal Rh status even when the mother or the fetus have the RhD psi genotype.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. The materials, methods, and examples are illustrative only and not intended to be limiting.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. The recitation of ranges of values herein is merely intended to serve as a shorthand method of referring individually to each separate value falling within the range. To facilitate review of the various embodiments of this disclosure, the following explanations of specific terms are provided:

Administer or Apply: To provide or give a subject a composition, such as a pharmaceutical composition, by an effective route. Exemplary routes of administration include, but are not limited to, parenteral, topical, transdermal, oral, intravenous, and muscular routes.

Analog: A compound having a structure similar to another, but differing from it, for example, in one or more atoms, functional groups, or substructure.

Antibody: An immunoglobulin capable of specifically binding a target molecule, such as a carbohydrate, a polynucleotide, a lipid, or a polypeptide, via one or more antigen recognition sites, located in the variable region of the immunoglobulin molecule. The term "antibody" includes polyclonal and monoclonal antibodies, fragments thereof, such as Fab, Fab', F(ab')2 and Fv, single chain variable fragments (ScFv), mutants thereof, fusion proteins comprising an antibody portion, and any other modified configuration of the immunoglobulin molecule that comprises an antigen recognition site. Antibodies can be distinguished into five major classes, IgA, IgD, IgE, IgG, and IgM, according to the amino acid sequence of the constant domain in their heavy chains. Monoclonal antibodies are obtained from a substantially homogeneous population of antibodies, and specifically target a single epitope (determinant) of an antigen. Polyclonal antibodies target different epitopes on the antigen. The heavy and light chains of an antibody each comprise a variable region and a constant region. The variable regions of the heavy and light chain each consist of four framework regions (FR) connected by three complementarity-determining regions (CDRs), also known as hypervariable regions. The CDRs in each chain are held together in close proximity by the FRs and form the antibody's antigen-binding site. The constant regions of the heavy and light chains of an antibody provide structural stability and are not involved in antigen binding.

Binding Site or Binding Domain: A region on a protein, DNA or RNA, to which specific molecules and/or ions (ligands) may form a chemical bond. Characteristics of binding sites are chemical specificity, a measure of the types of ligands that will bond, and affinity, which is a measure of the strength of the chemical bond.

Congenital Disorder: A condition or disease present at birth, which is inherited or brought about by environmental factors, such as the mother's alcohol or drug consumption, nutritional intake and placental health. Examples of congenital disorders include, but are not limited to, congenital heart defect, cleft lip, sickle cell disease, alpha-thalassemia, beta-thalassemia, spinal muscular atrophy, spina bifida and Down syndrome.

Contacting: Placement in direct physical association; includes both in solid and liquid form. Contacting can occur in vitro with isolated cells (for example in a tissue culture dish or other vessel) or in vivo by administering an active agent to a subject.

Control: A reference standard of a known value or range of values.

Down Syndrome: A genetic disease that occurs when a person has a full or partial extra copy of chromosome 21 Down syndrome includes Complete trisomy 21, which is the most common chromosomal abnormality seen in children; Translocation trisomy 21, which occurs when two chromosomes, one of which is chromosome 21, join together at the ends, creating two independent number 21 chromosomes as well as a number 21 chromosome attached to another chromosome; and mosaic trisomy 21, a rare form of Down syndrome, where only some cells have an extra copy of chromosome 21.

Drug or Active Agent: A chemical substance or compound that induces a desired pharmacological or physiological effect, and includes therapeutically effective, prophylactically effective, or systematically effective agents.

Effective amount: The amount of an active agent (alone or with one or more other active agents) sufficient to induce a desired response, such as to prevent, treat, reduce and/or ameliorate a disorder.

Localized application: The application of an active agent in a particular location in the body.

Parenteral: A type of administration that includes subcutaneous injections, intravenous, intramuscular, intrasternal injection or infusion techniques. Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use.

Subject: A living multi-cellular vertebrate organism, a category that includes human and non-human mammals.

Surface or Body Surface: A surface located on the human body or within a body orifice.

Topical administration: Delivery of an active agent to a body surface, such as, the skin or mucosa.

Transdermal: A route of administration by which active ingredients are delivered across the skin for systemic distribution. Examples include transdermal patches for drug delivery.

Next Generation Sequencing-Based Non-Invasive Prenatal Test for Fetal Rhesus Determination and Fetal DNA Fraction Measurement In the United States, pregnant women who are identified as having an RhD negative blood type are prophylactically treated to prevent maternal production of RhD antibodies by receiving anti-D immunoglobulin (Rhogam shot) at week 28 and again after birth, regardless of the RhD blood type of their unborn babies.

High-throughput non-invasive pregnancy tests able to determine the RhD blood type of the unborn baby at an early stage of pregnancy can prevent unnecessary Rhogam shot administration to RhD-negative women who carry an RhD-negative fetus, and their exposure to inherent risks associated with the procedure. Furthermore, early fetal blood type determination gives piece of mind to doctors who perform amniocentesis and provide prenatal care.

Currently available high-throughput NIPT for fetal RhD status determination uses real-time quantitative polymerase chain reaction (PCR) technology to analyze fragmented DNA that is released by the placenta as cell-free DNA in the maternal blood circulation. These tests are based on the principle that a woman who tests RhD negative does not have a copy of the RHD gene, and therefore, the presence of an RHD gene in cell-free DNA suggests an RhD-positive fetus.

However, these tests may commonly be administered only at a late stage of pregnancy, at week 20 or later. This is because the fetal fraction frequently constitutes as low as 2% or lower of the cell-free DNA at a gestational age between 10 and 20 weeks. In these early gestational age samples, the low levels of fetal RhD molecules may not be detected by existing assays in weeks 10-20. If the fetal fraction is not known, the samples may be incorrectly called as negative for the RhD gene, even if the fetus is Rh positive. Accordingly, a 20-week threshold is usually required. Because of the 20-week threshold, fetal Rh status may not be known when potential bleeding events occur prior to Rhogam administration at week 28, and these events may cause sensitization by bringing maternal blood in contact with the fetus. Furthermore, current NIPTs suffer from low performance and high incidence of undetermined (no-call) results due to the absence of a fetal fraction measurement.

Moreover, these tests are not well suited for the analysis of mutated variations of the RHD gene, such as the presence of RHD pseudogene ψ. While the majority of RhD-negative individuals with white European ethnicity have no RHD gene, people with African ethnicity that have the Rh-negative phenotype frequently have a mutated gene that contains RhD sequences, but does not produce the D antigen. People with African ethnicity may therefore have the RHD pseudogene or the hybrid RHD-CE-D($^s$) gene. Currently available NIPTs could reveal an RhD-positive type for an RHD pseudogene, but serology tests would characterize the sample as RhD negative because of the abundant but untranslated maternal D gene sequences that are amplified, and thus lead to high rates of false-positive results.

Last but not least, these tests are expensive and generally not covered by health insurance in many countries, including in the United States.

Early and accurate determination of fetal blood type and fetal fraction is essential for appropriate prevention strategies. Precise estimation of the fetal fraction is crucial for accurate testing, confirmation and further prenatal diagnosis and treatment. The present inventors have developed a high-throughput and cost-efficient NIPT methodology that allows low-cost, accurate determination of fetal blood type and fetal fraction in one single assay. The disclosed NIPT combines multiplex PCR analysis with next generation sequencing to simultaneously amplify and then sequence selected polymorphic allele loci and multiple RhD gene locations to accurately measure fetal fraction and fetal RhD quantity, and use the fetal fraction and fetal RhD data to determine the fetal Rhesus D genotype.

Thus, provided herein are sequencing-based methods for accurate determination of fetal Rhesus D genotype and measurement of fetal fraction that can be performed in one assay at an early stage of pregnancy.

In some embodiments, the disclosed method comprises: (i) collecting a blood sample from a pregnant woman subject; (ii) extracting cell-free DNA from the blood sample; (iii) performing multiplex polymerase chain reaction of the cell-free DNA to simultaneously amplify polymorphic allele loci and multiple RhD gene locations; (iv) sequencing amplified DNA; (v) identifying and selecting polymorphic paternal alleles to obtain a fetal fraction measurement; (vi) identifying and selecting amplified RhD gene regions to obtain quantitative fetal RhD data; and (vii) combining the fetal fraction measurement and the fetal RhD amount data into an algorithm to determine the fetal Rhesus D genotype.

In some embodiments, the disclosed method comprises: (i) collecting a blood sample from a pregnant woman subject; (ii) extracting cell-free DNA from the blood sample; (iii) amplifying cell-free DNA in at least one RhD gene location in Exon 4 or Exon 5 or Exon 6, which is expected to differ between RhD positive and RHDψ genotype; (iv) simultaneously amplifying cell-free DNA at a plurality of polymorphic allele loci; (v) sequencing amplified DNA; (vi) identifying and selecting polymorphic paternal alleles to obtain a fetal fraction measurement; (vii) classifying sequencing data from the RhD gene regions as belonging to RhD or RHDψ sequence; (vii) quantifying the levels of RhD and RHDψ; and (viii) combining fetal fraction measurement and levels of fetal RhD data and fetal RHDψ data into an algorithm to differentiate between fetal RhD positive, fetal RhD negative, and fetal RHDψ genotypes.

In other embodiments, the disclosed method comprises: (i) collecting a blood sample from a pregnant woman subject; (ii) extracting cell-free DNA from the blood sample; (iii) performing simultaneous amplification of the cell-free DNA at multiple RhD gene locations; (iv) sequencing amplified DNA; (v) identifying and selecting amplified RhD gene regions to obtain quantitative fetal RhD data; and (vi) determining fetal Rhesus D genotype.

In some embodiments, the disclosed method may further comprise (vi) amplifying polymorphic allele loci; (vii) sequencing amplified DNA; and (viii) identifying and selecting polymorphic paternal alleles to obtain a fetal fraction measurement.

Sequencing associated with one or more embodiments includes high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SNRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. Additionally, or alternatively, sequencing can include any suitable sequencing technologies (e.g., Sanger sequencing, capillary sequencing, etc.).

Amplification of cell-free DNA associated with one or more embodiments can include performing any one or more of: PCR-based techniques (e.g., solid-phase PCR, RT-PCR, qPCR, multiplex PCR, touchdown PCR, nanoPCR, nested PCR, hot start PCR, universal amplification of ligated sequences etc.), helicase-dependent amplification (HDA), loop mediated isothermal amplification (LAMP), self-sustained sequence replication (3 SR), nucleic acid sequence based amplification (NASBA), strand displacement amplification (SDA), rolling circle amplification (RCA), ligase chain reaction (LCR), and/or any other suitable amplification techniques and/or associated protocols (e.g., protocols for minimizing amplification bottlenecking). In an example, generating an amplified cell-free DNA mixture can include performing a plurality of PCR rounds to amplify the target-associated molecules with the target molecules (e.g., using primers targeting a sequence shared by both the target-associated molecules and the target molecules). In a specific example, the amount of amplification (e.g., number of PCR rounds, cycles, etc.) can be performed according to results of validation experiments (e.g., during primer selection and validation, stopping PCR reactions at different amplification cycles and visualizing products by gel electrophoresis to determine adequacy of amplification for conditions and/or applications described herein, such as sufficient amplification for NGS while minimizing saturation to facilitate preservation of ratios; etc.). In specific examples, generating amplified cell-free DNA mixtures can include subsampling the biological sample into different subsamples designated for different target molecule types and a target-associated molecule type, each pair corresponding to a different target regions (e.g., of the RhD gene, of locations of polymorphic variants, or chromosome 21, etc.) and/or different target; and amplifying the different subsamples (e.g., through sets of PCR rounds) by using primers specific to the pair corresponding to the subsample. Additionally or alternatively, target molecules and target-associated molecules for multiple pairs of a target molecule type (e.g., associated with a plurality of different targets, etc.) may be amplified in the same tube (and/or any suitable number of tubes), such as through multiplex PCR, which can facilitate conserving a precious sample; an amplified target molecule and target-associated molecule pair may then be selectively sequenced via a sequencing oligonucleotide that is specific to the target pair. In this or other examples, subsampling and/or other sample modification operations can be performed in any suitable order.

Quantification metrics can include any one or more of counts (e.g., sequence read count; absolute molecule count; counts of target-associated molecules; counts for biological targets, such as for target molecules corresponding to the biological targets; counts for reference-associated molecules; counts for biological references, such as for reference molecules corresponding to the biological references; etc.); ratios (e.g., a target-associated count ratio of a count for a biological target to a count for target-associated molecules; a reference-associated count ratio of a count for a biological reference to a count for reference-associated molecules; ratios with any suitable numerator and denominator associated with counts and/or other suitable quantification metrics; etc.); individual quantification metrics (e.g., individual quantification metrics such as individual counts for pairs of target-associated region type and target sequence region type; individual counts for individual samples; individual quantification metrics such as individual counts for different types of molecules, targets, references, described herein; etc.); overall quantification metrics (e.g., based on individual quantification metrics; overall target-associated count ratios; overall reference-associated count ratios; etc.); relative quantifications; absolute quantifications; and/or other suitable quantification metrics. Quantification metrics associated with target molecules and/or biological targets (e.g., a target-associated count ratio) can preferably be compared to quantification metrics associated with reference molecules and/or biological references (e.g., a reference-associated count ratio), which can facilitate relative quantification analyses (e.g., in screening for conditions associated with aneuploidy; for suitable comparisons usable in characterization of one or more conditions; etc.).

The methods provided herein may further comprise, within the same assay, quantifying fetal molecules in the RhD gene regions; analyzing the blood sample to determine the fetus' sex and/or analyzing the blood sample to determine presence or absence of fetal aneuploidy for genetic disease detection. Genetic diseases that may be detected by the disclosed method may include, but are not limited to, Down syndrome, Edwards syndrome, Patau syndrome, Turner syndrome, and Klinefelter syndrome.

The disclosed NIPT methodology allows detection of fetal RhD molecules by amplifying multiple regions on the RHD gene. For example, five regions of the RHD gene may be analyzed: exon 4 in two separate locations, and exons 5,7 and 10. This procedure allows detection of the RHD pseudogene and other variants of the RHD gene. In addition, in order to assure high-test performance and prevent false positive signals, a fetal fraction measurement of the sample in the same multiplex PCR reaction is performed by amplifying 76 polymorphic alleles, approximately 25% of which contain a variant inherited solely from the father, and therefore unique to the fetus. Quantitative determination of the unique fetal variants, i.e., informative loci, is then used to determine the fetal fraction value. An average, i.e., mean or median, of up to 9 informative polymorphic loci can then be used to determine the fetal fraction. The fetal fraction value thus obtained is then inserted into an algorithm together with the quantitative value obtained for the fetal RhD molecules to determine the RhD blood type of the fetus.

The disclosed NIPT methodology affords significant advantages over existing technologies. The disclosed NIPT allows reliable determination of polymorphic allele variations that are unique to the fetus at a young gestational age, and it may therefore be administered as early as at week 10 of pregnancy. Moreover, quantification of fetal RhD molecules along with the determination of the fetal fraction in a single assay results in extremely accurate, high quality data at a very early stage of pregnancy, and thus increase the sensitivity and specificity of the assay, while decreasing no-call results. Furthermore, the combination of next generation sequencing with multiplex PCR analysis drastically reduces background noise, eliminates waste of precious cell-free DNA samples and decreases costs associated with testing. In addition, sex determination for parental knowledge and genetic screening may be performed as part of the same assay, thus allowing early intervention and clinical decisions when needed.

The disclosed NIPTs can therefore be safely and reliably administered to pregnant women who are at a gestational stage between 10 and 12 weeks. The pregnant women may have Rhesus D negative genotype, Rhesus RhD-CE-D genotype, or Rhesus D pseudogene (RHDψ) genotype.

Thus, unlike traditional existing technologies, the disclosed NIPT methodology allows early and accurate determination of fetal fraction, fetal molecules, fetal blood type and, optionally, fetal sex and genetic screening in one simple assay.

EXAMPLES

Example 1: Determination of Fetal RhD Blood Type and Measurement of Fetal Fraction Plasma samples of pregnant women with RhD-negative blood type at 10 week or older gestational age were obtained. The plasma samples were purified to extract the cell-free DNA (cfDNA) from each sample. 67 cfDNA samples thus obtained were subjected to combined Rh NIPT and Fetal Fraction assay. The cell free DNA of each sample was amplified by multiplex PCR using a customized amplicon panel that targeted 76 polymorphic alleles for fetal fraction measurement and 5 amplicons within the RhD gene to determine the presence or absence of the RhD gene. The five regions within the RhD gene included exons 4 in two different locations, 5, 7 and 10. Since the mothers were RhD-negative, RhD amplicon detection indicated that the fetus had RhD-positive blood type. The samples were subjected to additional PCR reactions to attach sequencing and indexing DNA sequences, and the amplified DNA was then sequenced on a sequencer.

Sequencing data was classified as belonging to polymorphic allele locations, RhD locations or RhDψ locations via alignment to a custom-built version of the human genome. This custom genome was constructed by concatenating the sequences of the RhD psudogene to the human reference genome build GRCH37. Alignment was performed by employing a Burrows-Wheeler transform using the bwa-mem computer program. Individual based quality scores (PHRED) scores where then analyzed where PHRED_score=$-10*\log_{10}(P)$ where is P is the probability base-calling error. Specifically, the bases that differ between the RhD gene and the RhD psudogene were examined and sequencing reads in which these bases had PHRD scores less than a cutoff of 35 were eliminated. Counts of sequencing reads aligning to each of the RhD and RhD amplicons were then quantified using the bedtools coverage computer program.

For fetal fraction determination, sequencing read alignment was performed as described above. Variant calling was performed on the sequencing data using the samtools mpileup computer program. The allele fraction of each variant was calculated as the percent of minor variant sequencing reads as a percent to total sequencing reads at that location. Polymorphic paternal alleles were identified as variants whose allele fraction was less than 20% and unlikely to derived from sequencing error. The fetal fraction of the samples was then calculated as twice the median allele frequency of up to 9 chosen paternal alleles.

A measurement of the total amount of cell-free DNA was made and combined with the fetal fraction in order to develop a per-sample expectation of the abundance of paternal RhD levels. The number of cell-free DNA molecules present in each sample was calculated at a secondary location on chromosome 11, which is unrelated to RhD variants, using the quantification approach described above. The expected number of paternal RhD molecules was then calculated in each sample using the number of cfDNA molecules and the fetal fraction data thus obtained, using the formula
rhd_molecules=chromosome_11_molecules*fetal_fraction/2.

For fetal RhD blood type determination, the cell free DNA in each sample was amplified using 5 amplicons within the RhD gene to determine the presence or absence of the RhD gene. The five regions within the RhD gene included exons 4 in two different locations, 5, 7 and 10. The amplicons on exons 4 and 5 amplified regions known to vary between the RhD gene and the RhD pseudogene. Since the mothers were RhD-negative, RhD amplicon detection indicated that the fetus had RhD-positive blood type.

The number of RhD molecules at each of the 5 locations within the RhD gene was calculated as described above, and normalized against the expected number of paternal RhD molecules, as calculated using the fetal fraction and the cell-free DNA amount present based on chromosome 11 above. Normalization to the total cell-free DNA amount controls for variation in the amount of cell-free DNA obtained from different patients. Additional normalization of the fetal fraction controls for variation in the fraction of DNA arising from the fetus which can range from 0.5% to 25% in pregnant mothers (i.e., ~0.25% to ~12.5% paternal allele fraction). Controlling for these two properties on a per-sample basis increased the sensitivity, increased the specificity and reduced the no-call rate of the assay.

Figure 1:
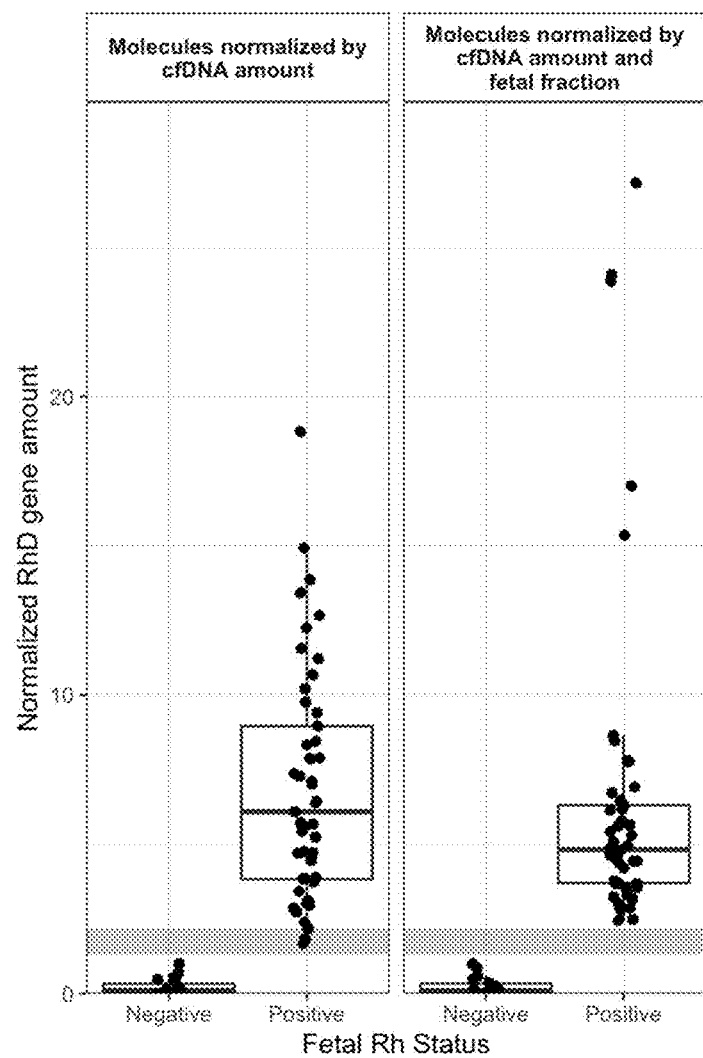
FIG. 1 shows the results of the experiment described in Example 1. Each data point indicates the value obtained for the second most abundant RhD amplicon for each sample. A sample whose second most abundant amplicon had a value below the shaded region was classified as an RhD-negative blood type sample. A sample whose second most abundant amplicon had a value above the shaded region was classified as an RhD-positive blood type sample. A sample whose second most abundant amplicon had a value within the shaded region was classified as an RhD-unidentified blood type sample. The plot on the left shows the results obtained from counts that were normalized only against cfDNA amounts. The plot on the right shows the results obtained from counts that were normalized against cfDNA amounts and against fetal fraction data. Comparison of the two plots indicates that without fetal fraction normalization there are multiple no-calls (6% no-call rate), whereas normalization by fetal fraction allows RhD blood type classification of all samples and eliminates no-call results (0% no-call rate). The right plot also shows the high performance of the assay.

After normalization was performed, the value of the second most abundant RhD amplicon for each sample was then plotted to measure the amount of RhD present and determine the RhD blood type, as shown in FIG. 1. A sample whose second most abundant amplicon had a value below the shaded region was classified as an RhD-negative blood type sample. A sample whose second most abundant amplicon had a value above the shaded region was classified as an RhD-positive blood type sample. A sample whose second most abundant amplicon had a value within the shaded region was classified as an RhD-unidentified blood type sample. The plot on the left side of the figure shows the results obtained from counts that were normalized only against cfDNA amounts. The plot on the right side shows the results obtained from counts that were normalized against cfDNA amounts and against the fetal fraction. Comparison of the two plots indicates that without fetal fraction normalization there are multiple no-calls (6% no-call rate), whereas normalization by fetal fraction allows RhD blood type classification of all samples and eliminates no-call results (0% no-call rate). The right plot also shows the high performance of the assay. These data show that fetal fraction measurement in combination with RhD detection is critical to implementing a high performing Rh NIPT, which performs at early gestational ages below 20 weeks as well as at gestational ages of 20 weeks or later.

FIG. 2 shows the performance of the assay for each of the 5 amplicons within the RhD gene in all tested samples. The bars represent the mean amount of RhD amplicon measured for each sample. Error bars represent the standard mean error for each sample. The data show the large difference in signal between RhD-negative fetal blood type and RhD-positive fetal blood type for each of the amplicons that were tested in this assay.

Example 2: Use of Fetal Fraction and Level of Cell-Free DNA for Fetal Sex Determination and Genetic Disease Detection The samples obtained as described in Example 1 are further analyzed to determine the sex of the fetus and the presence or absence of aneuploidy for genetic disease detection in the same single assay. Genetic diseases that are detected by the NIPT include Down syndrome, Edwards Syndrome, Patau Syndrome, Turner syndrome, Klinefelter syndrome as well as single-gene disorders such as cystic fibrosis, sickle cell disease, spinal muscular atrophy, and thalassemias.

Example 3: Detection of Fetal RhD Psi Variant Blood Type

In the Caucasian population, RhD-negative blood type is predominantly due to homozygous deletion of the RhD gene. In black African populations, the RhD-negative blood phenotype is predominantly due to the presence of the RhD pseudogene psi variant. Most available tests for determination of fetal RhD blood type fail to detect the psi variants and provide no-call results.

An algorithm was developed to differentially analyze samples for the presence of RhD when the RhD pseudogene psi variant was found to be present and is summarized in FIG. 3. Data was analyzed as described in Example 1 for the unique amplicons generated by the RhD psi variant in two locations in exon 4 and in one location in exon 5. The use of sequencing technology uniquely enables this assay to differentiate between RhD and the RhD psi pseudogene. If RhD psi sequence was detected as present in any of these locations the sample underwent a separate set of statistical analyses that tested the presence of the Rh+RhD gene at locations only in exons 4 and exon 5. This is because the RhD psi gene contains sequence identical to the RhD gene in exons 7 and 10. This algorithm allowed for accurate determination of fetal Rh status even when the mother or the fetus have the RhD psi genotype.

To determine whether the disclosed NIPT assay can detect RhD psi variants at an early stage of pregnancy, plasma samples of pregnant black and white African women at 10 week or older gestational age are obtained and analyzed to measure fetal fraction and determine RhD blood type as described in Example 1. It is found that 3 out of 30 fetuses have RhD-ψ blood type. These results show that the disclosed NIPT assay can detect even the rarer forms of RhD variants, which further increases the usefulness of fetal Rh determination.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

The invention claimed is:

1. A non-invasive method for accurate determination of fetal Rhesus D genotype and measurement of fetal fraction in one assay at an early stage of pregnancy, wherein the method comprises:
   (i) collecting a blood sample from a pregnant woman subject;
   (ii) extracting cell-free DNA from the blood sample;
   (iii) performing multiplex polymerase chain reaction of the cell-free DNA to simultaneously amplify polymorphic allele loci and multiple RhD gene locations;
   (iv) sequencing amplified DNA;
   (v) choosing polymorphic alleles from the sequenced amplified DNA whose allele fraction is less than a predetermined percentage;
   (vi) averaging the allele fraction for a plurality of the chosen polymorphic alleles to determine a fetal fraction;
   (vii) quantifying total cell free DNA;
   (viii) multiplying fetal fraction and the total cell free DNA to determine an expected number of fetal molecules in the blood sample;
   (ix) determining a per sample normalization based on the expected number of fetal molecules in the blood sample;
   (x) computationally aligning sequencing reads to a human reference genome using a Burrows-Wheeler algorithm;
   (xi) identifying and selecting amplified RhD gene regions to obtain quantitative fetal RhD data;
   (xii) determining the fetal Rhesus D genotype by applying the per sample normalization to the quantitative fetal RhD data and comparing the normalized result with a predetermined value for the Rhesus D genotype; and
   (xiii) administering anti-D immunoglobulin to the pregnant woman where the pregnant woman has an Rh-D negative blood type and the determined fetal Rhesus D genotype is an Rh-D-positive blood type.

2. The method of claim 1, wherein the pregnant woman subject is at a gestational stage between 10 and 20 weeks.

3. The method of claim 1, wherein the pregnant woman subject is at 20 weeks or later stages of gestation.

4. The method of claim 1, wherein the pregnant woman subject has Rhesus D negative genotype.

5. The method of claim 1, wherein the pregnant woman subject has Rhesus RhD-CE-D genotype.

6. The method of claim 1, wherein the pregnant woman subject has Rhesus D pseudogene (RHDO genotype.

7. The method of claim 1, wherein the method further comprises analyzing the blood sample to determine the fetus' sex.

8. The method of claim 7, wherein the method further comprises analyzing the blood sample to determine presence or absence of fetal aneuploidy for genetic disease detection.

9. A non-invasive method for accurate determination of fetal Rhesus D genotype and measurement of fetal fraction in one assay at an early stage of pregnancy, wherein the method comprises:
   (i) collecting a blood sample from a pregnant woman subject;
   (ii) extracting cell-free DNA from the blood sample;
   (iii) performing multiplex polymerase chain reaction of the cell-free DNA to simultaneously amplify polymorphic allele loci and multiple RhD gene locations;
   (iv) sequencing amplified DNA;
   (v) choosing polymorphic alleles from the sequenced amplified DNA whose allele fraction is less than a predetermined percentage;
   (vi) averaging the allele fraction for a plurality of the chosen polymorphic alleles to determine a fetal fraction;
   (vii) quantifying total cell free DNA;
   (viii) multiplying fetal fraction and the total cell free DNA to determine an expected number of fetal molecules in the blood sample;
   (ix) determining a per sample normalization based on the expected number of fetal molecules in the blood sample;
   (x) identifying and selecting amplified RhD gene regions to obtain quantitative fetal RhD data;
   (xi) determining the fetal Rhesus D genotype by applying the per sample normalization to the quantitative fetal RhD data and comparing the normalized result with a predetermined value for the Rhesus D genotype; and
   (xii) administering anti-D immunoglobulin to the pregnant woman where the pregnant woman has an Rh-D negative blood type and the determined fetal Rhesus D genotype is an Rh-D-positive blood type.

10. The method of claim 9, wherein the pregnant woman is at a gestational period from 10 weeks to 20 weeks.

11. The method of claim 9, wherein the pregnant woman subject is at 20 weeks or later stages of gestation.

12. The method of claim 9, wherein the pregnant woman subject has Rhesus D negative genotype.

13. The method of claim 9, wherein the pregnant woman subject has Rhesus RhD-CE-D genotype.

14. The method of claim 9, wherein the pregnant woman subject has Rhesus D pseudogene (RHDψ) genotype.

15. The method of claim 9, wherein the method further comprises analyzing the blood sample to determine the fetus' sex.

16. The method of claim 15, wherein the method further comprises analyzing the blood sample to determine presence or absence of fetal aneuploidy for genetic disease detection.

* * * * *

UNITED STATES PATENT AND TRADEMARK OFFICE
CERTIFICATE OF CORRECTION

| | | |
|---|---|---|
| PATENT NO. | : 11,946,104 B2 | Page 1 of 1 |
| APPLICATION NO. | : 16/923005 | |
| DATED | : April 2, 2024 | |
| INVENTOR(S) | : Landry et al. | |

It is certified that error appears in the above-identified patent and that said Letters Patent is hereby corrected as shown below:

In the Claims

In Column 14, in Claim 6, Line 4, delete "(RHDO" and insert -- (RHDΨ) --, therefor.

Signed and Sealed this
Eleventh Day of June, 2024

Katherine Kelly Vidal
*Director of the United States Patent and Trademark Office*